United States Patent
Lan et al.

(10) Patent No.: US 11,458,219 B2
(45) Date of Patent: Oct. 4, 2022

(54) UV LIGHT AND STERILIZATION SYSTEM

(71) Applicant: SHENZHEN GUANKE TECHNOLOGIES CO., LTD, Shenzhen (CN)

(72) Inventors: Qing Lan, Shenzhen (CN); Ligen Liu, Shenzhen (CN); Shoubao Chen, Shenzhen (CN); Tianlong Dai, Shenzhen (CN); Buyuan Peng, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 209 days.

(21) Appl. No.: 16/897,693

(22) Filed: Jun. 10, 2020

(65) Prior Publication Data

US 2021/0330829 A1     Oct. 28, 2021

(30) Foreign Application Priority Data

Apr. 24, 2020   (CN) .......................... 202020649572.3

(51) Int. Cl.
  *A61L 2/10* (2006.01)
  *F21V 23/06* (2006.01)
  *F21V 15/01* (2006.01)

(52) U.S. Cl.
  CPC ................ *A61L 2/10* (2013.01); *F21V 15/01* (2013.01); *F21V 23/06* (2013.01); *A61L 2202/11* (2013.01)

(58) Field of Classification Search
  CPC .... A61L 2/10; A61L 2202/11; A61L 2202/16; A61L 9/20; C02F 1/325
  See application file for complete search history.

(56) References Cited

U.S. PATENT DOCUMENTS

2017/0340760 A1* 11/2017 Starkweather ............ A61L 2/24
2019/0060505 A1*  2/2019 Jaworski .................. A61L 2/202
2021/0330828 A1* 10/2021 Lan .......................... G01V 8/10

* cited by examiner

*Primary Examiner* — Eliza W Osenbaugh-Stewart
(74) *Attorney, Agent, or Firm* — Maier & Maier, PLLC

(57) ABSTRACT

A UV light and sterilization system. The UV light includes: a base, a reflex lamp housing and several UV modules; the reflex lamp housing is provided on the base, the periphery of the reflex lamp housing is provided with several containing grooves, and the inner wall of each of the containing grooves is provided as a reflective panel; several the UV modules are provided on the base and connect to the base electrically, and each of the UV modules is contained in a the containing groove. The UV light provides UV illumination and improves sterilization effects.

14 Claims, 10 Drawing Sheets

UV LIGHT AND STERILIZATION SYSTEM

CROSS-REFERENCE TO RELATED APPLICATIONS

This application claims the priority of Chinese Patent Application No. 2020206495723 filed on Apr. 24, 2020, the disclosure of which is incorporated herein by reference.

FIELD

The embodiments relates to the technical field of sterilization equipment, particularly to a UV light and sterilization system using the UV light.

BACKGROUND

In daily application, disinfectant and ultraviolet rays can be used to realize environment sterilization. Wherein, sterilization with ultraviolet rays can avoid residual chemical agents and guarantee users' personal safety as possible. Commonly used UV germicidal light is a light bar which accesses the power grid via a bar base; Therefore, ultraviolet rays generated by a light bar can radiate to all directions of the light bar, and, as a result, partial ultraviolet rays will radiate onto bar base, partial ultraviolet rays are absorbed by the bar base, so that illumination of ultraviolet rays radiating to the environment is insufficient, and environment sterilization is not effective.

The foregoing content is only used for assisting in understanding the technical scheme of the invention, but not mean the acknowledgement of that the above content is a prior art.

SUMMARY

A purpose of this invention is to provide a UV light to improve the UV sterilization coverage and enhance the UV sterilization effect.

In order to achieve the above purpose, the UV light provided includes:
a base;
the reflex lamp housing is provided on the base, the periphery of the reflex lamp housing is provided with several containing grooves, and the inner wall of each of the containing grooves is provided as a reflective panel; and
several UV modules provided in several the containing grooves and connecting to base electrically.

In one embodiment, the inner wall of the containing grooves is in a cambered shape.

In one embodiment, the UV light also comprises one protective lantern ring provided around the reflex lamp housing and provided at intervals with the base to form a light access area.

In one embodiment, the periphery of the reflex lamp housing is provided with three the containing grooves;
and/or, the reflex lamp housing is made of aluminum alloy;
and/or, the protective lantern ring is made of aluminum alloy.
and/or, the reflex lamp housing is of a sleeve structure;
and/or, the protective lantern ring is of a sleeve structure.

In one embodiment of this invention, the UV light also comprises a support plate provided on one end of the reflex lamp housing away from the base and provided with a locating hole corresponding to each of the containing grooves;
one end of each of the UV modules away from the base goes through the locating hole.

In one embodiment, the UV light also comprises several elastic washers, and each of the elastic washers is provided on one the locating hole;
the UV module goes through the locating hole, and dais elastic washer is clamped between the UV module and the inner wall of the locating hole.

In one embodiment, the UV light also comprises an inductive component provided on one side of the support plate back on to the reflex lamp housing and connecting to say base electrically via lead.

Wherein In one embodiment, one side of the support plate back on to the reflex lamp housing is provided with mounting grooves and through-holes connecting the mounting grooves;
the reflex lamp housing is provided with avoiding holes connecting the through-hole;
the inductive component is provided in the mounting groove, and the inductive component connects to say base via lead passing through the avoiding hole and the through-hole.

In one embodiment, the base comprises:
lamp housing provided with an installation cavity and several offsetting holes connecting to the installation cavity; and
circuit component provided in the installation cavity and provided with connection end corresponding to each of the offsetting holes;
the reflex lamp housing connects to say lamp housing, each of the containing grooves is provided corresponding to each of the offsetting hole, each of the UV modules passes through each of the offsetting holes and connects to say connection end electrically.

An embodiment also provides a sterilization system, characterized in comprising a remote control and the UV light, the remote control connects with the base of the UV light for communication;
where, the UV light includes:
a base;
the reflex lamp housing is provided on the base, the periphery of the reflex lamp housing is provided with several containing grooves, and the inner wall of each of the containing grooves is provided as a reflective panel; and
several UV modules provided in several the containing grooves and connecting to base electrically;
a remote control connecting to the base for communication.

The technical solution of this invention provides the reflex lamp housing on the base, the periphery of the reflex lamp housing is provided with several containing grooves, and the inner wall of each of the containing grooves is provided as a reflective panel; wherein, several the UV modules are provided in several containing grooves, that is, UV modules can connect to the base and/or reflex lamp housing, several the UV modules connect to the base electrically, taking the base as the connection base of accessing power, the base can provide power for several the UV modules, and several UV modules are provided in several containing grooves to send ultraviolet rays. Understandably, the base is a connection base, a reflex lamp housing is provided around the base to reduce the possibility that ultraviolet rays irradiate onto the base, so that ultraviolet rays can contact with air and articles in the environment sufficiently to improve the sterilization and disinfection efficiency; in another aspect, several UV modules send ultraviolet rays to enhance UV illumination within the unit time and enhance the coverage of rays of light, improve the UV sterilization efficiency and reduce UV sterilization time; in yet another aspect, the periphery of the reflex lamp housing is provided with several containing grooves, each of the containing grooves inside is provided with a UV module, so that several UV modules are provided around the reflex lamp housing, avoiding parallel setting of several UV modules, reducing dimensions of UV light and realizing a compact structure of the UV light; in yet another aspect, the containing groove are provided as a reflective panel, so that after several UV modules send ultraviolet rays, ultraviolet rays can be reflected by the inner wall of containing groove of reflex lamp housing to the environment to realize that the environment around UV light can be illuminated by ultraviolet rays, illumination of ultraviolet rays is improved, and the sterilization effect is improved.

BRIEF DESCRIPTION OF THE DRAWINGS

To better describe the technical schemes of the invention or prior art, a brief introduction of drawings to be used in the descriptions of the embodiment or prior art is made hereby. Obviously, the drawings described below are only several embodiments of the invention. For common technicians in this field, they can obtain other drawings based on these structures shown in the drawings without making additional creative endeavors.

DETAILED DESCRIPTION

Figure 1:
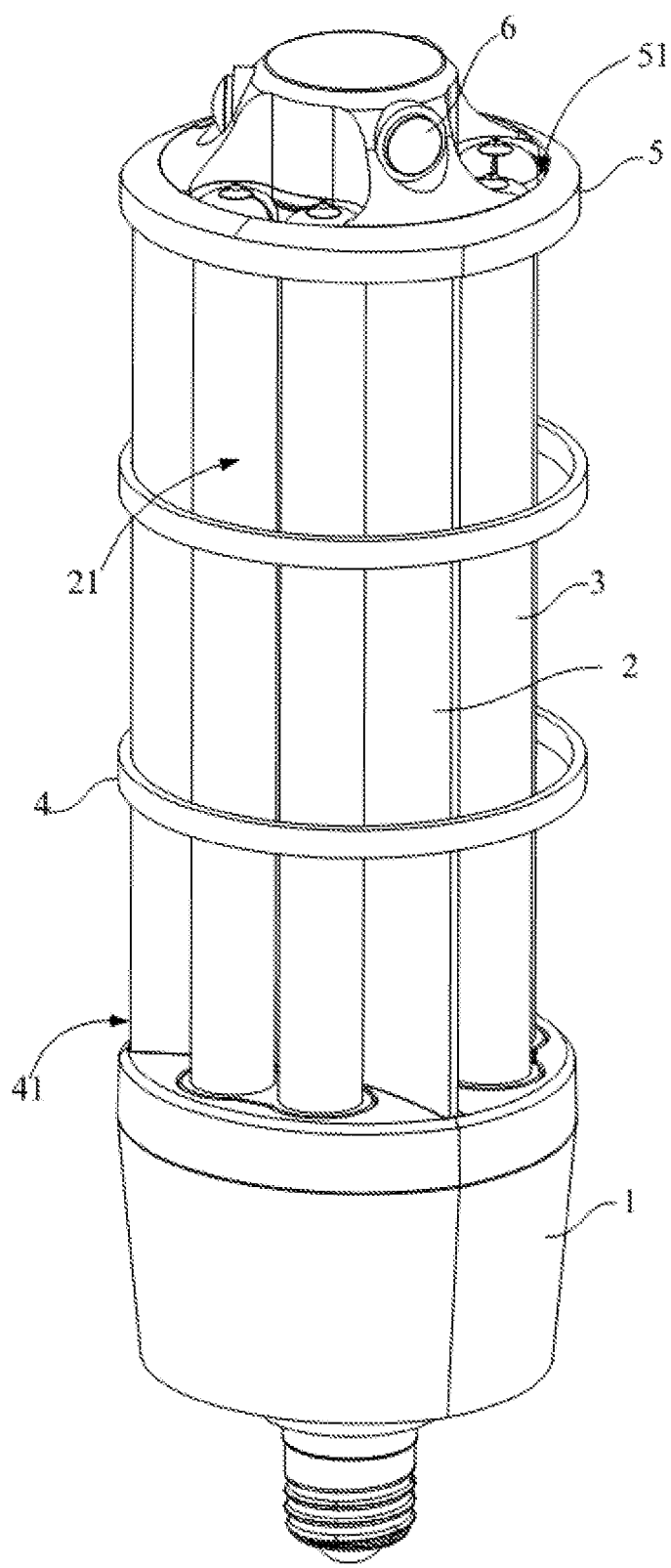
FIG. 1 is a schematic diagram showing the structure of an embodiment of UV light.

A clear and complete description of the technical schemes combined with the drawing in invention embodiments, this invention embodiments clearly and completely describe the technical programs. Obviously, only some embodiments of this invention (instead of all the utility model embodiments) are described here. Based on the embodiment of the invention, all other embodiments acquired by the common technicians in this field without creative work, shall be in the protection scope of this invention.

It should be noted that, if there is a directional indication (upper, lower, left, right, front, and rear, etc.) in the embodiment of the invention, the directional indication is only used to explain the relative positional relationship, motion condition, etc. between the components in a particular position (as shown in the drawing), and if the particular attitude is changed, the directional indication is changed accordingly.

In addition, if there are descriptions relating to "first", "second" and the like in embodiments of the invention, such descriptions of "first", "second" and the like are for descriptive purposes only and are not to be construed as indicating or implying their relative importance or implying an indication of the number of indicated technical features. As such, a feature that defines as "first", "second" may explicitly or implicitly include at least one of that features. In addition, the "and/or" as stated in the whole text should be understood as there are three paralleled schemes where scheme A, or scheme B or scheme A and scheme B can be met at the same time (taking "A and/or B as an example").

In addition, the technical schemes of embodiments may be combined with each other, but must be available for common technicians in this field, and when the combination of the technical scheme is contradictory or impossible, it should be considered that the combination of the technical scheme does not exist and not fall within the scope of the invention.

Figure 2:
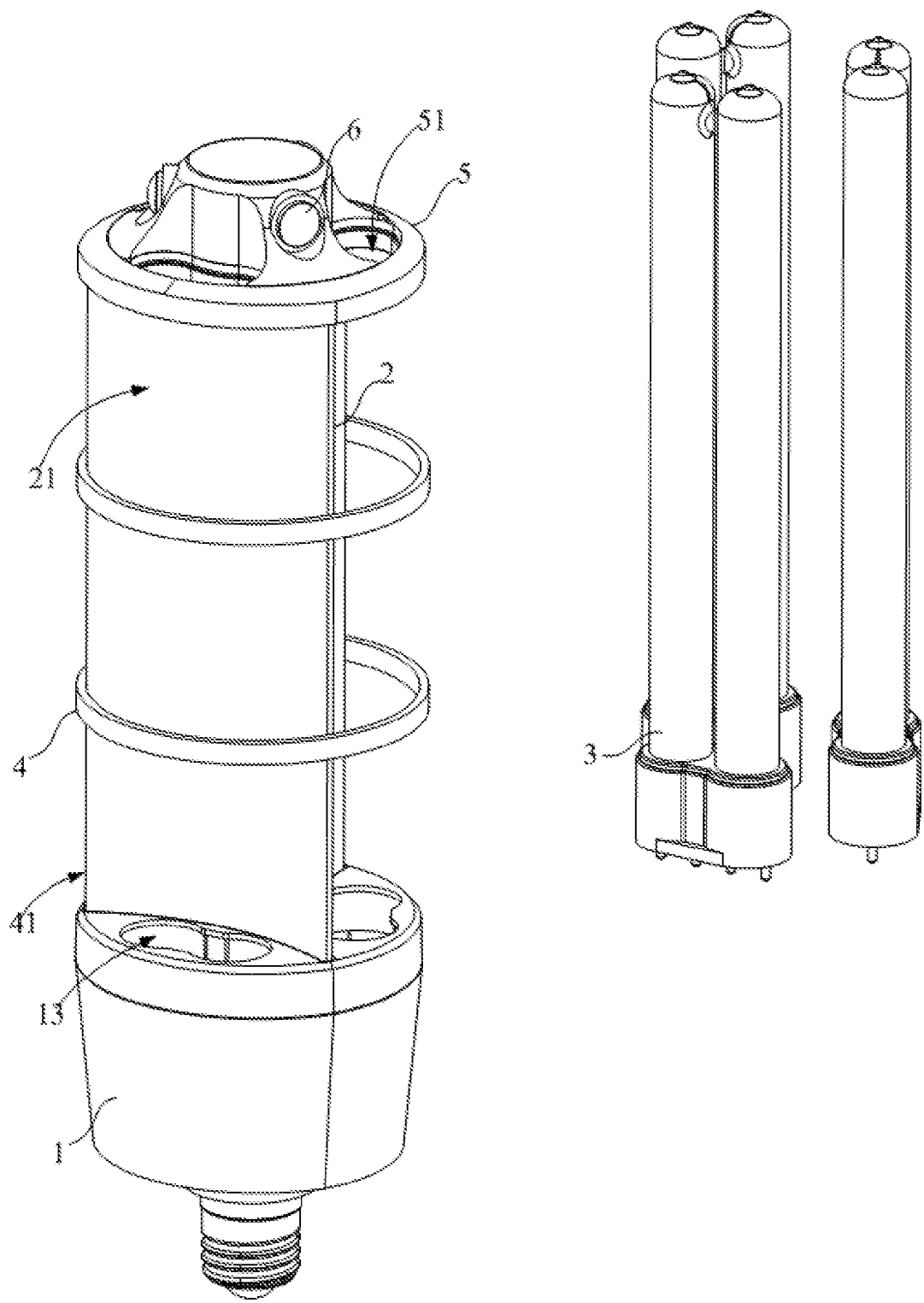
FIG. 2 is a schematic diagram showing the assembly structure of UV light in FIG. 1.
Figure 3:
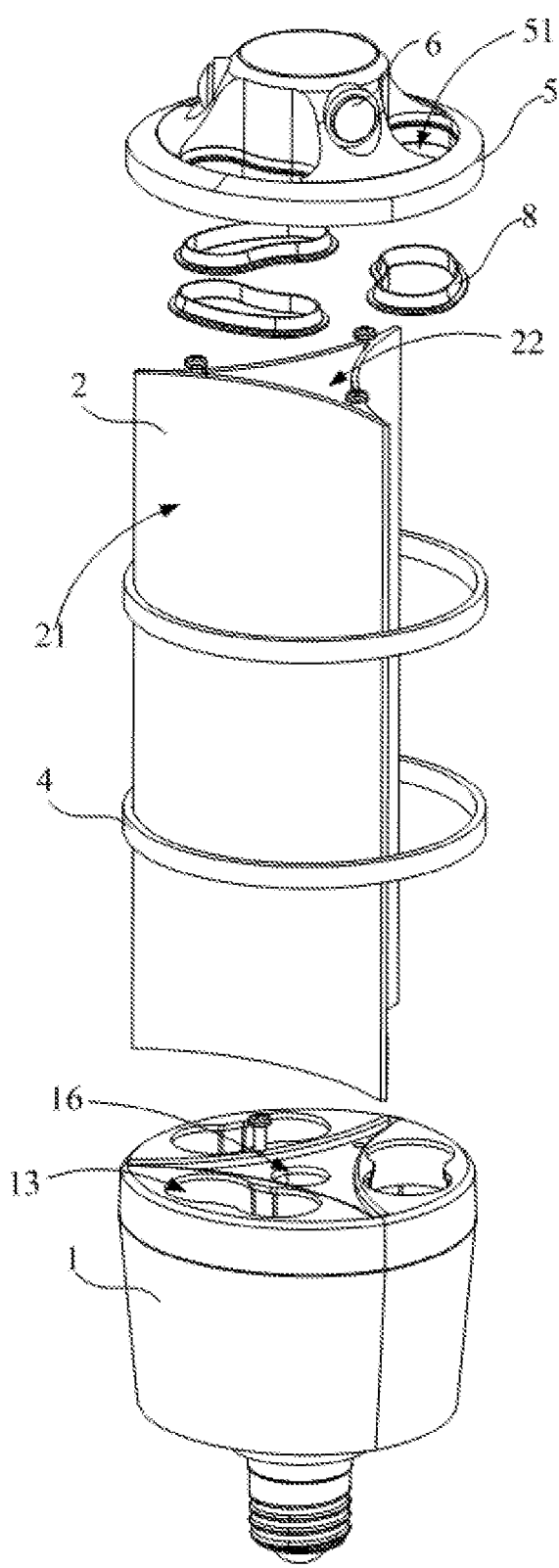
FIG. 3 is a schematic diagram showing the assembly structure of base and reflex lamp housing in FIG. 1.
Figure 4:
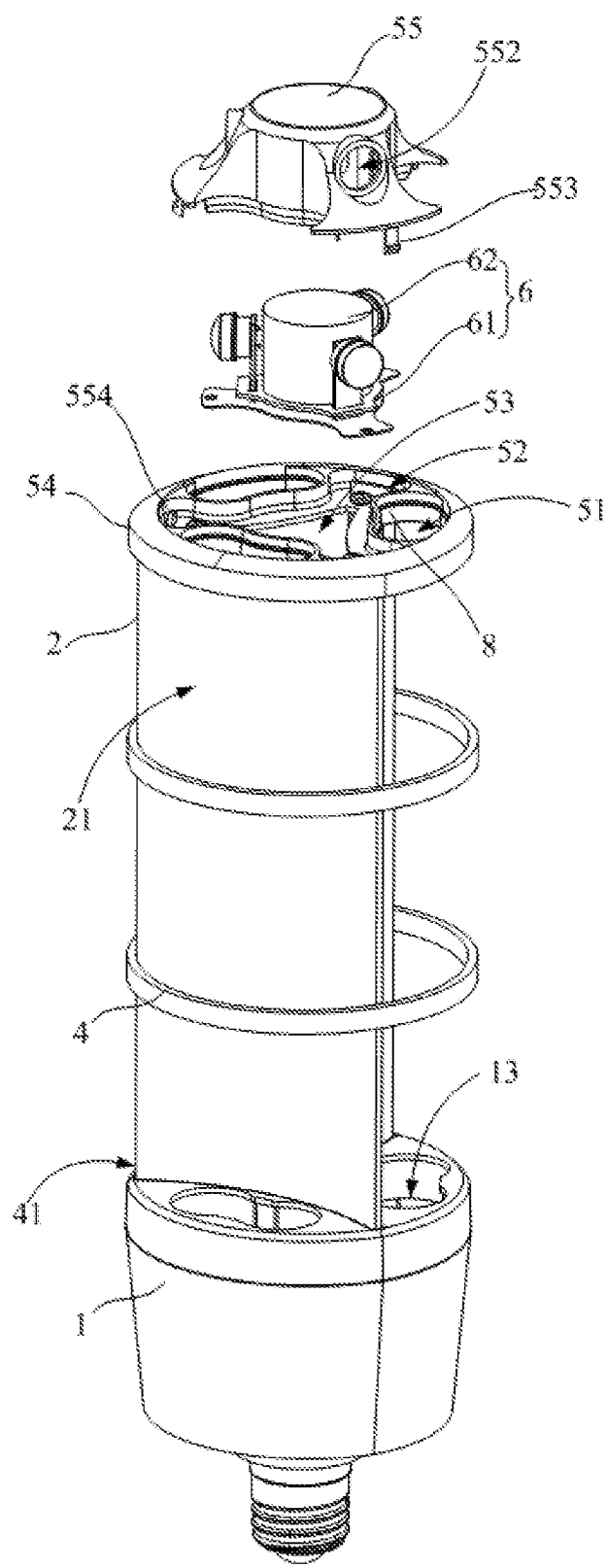
FIG. 4 is another schematic diagram showing the assembly structure of base and reflex lamp housing in FIG. 3.
Figure 5:
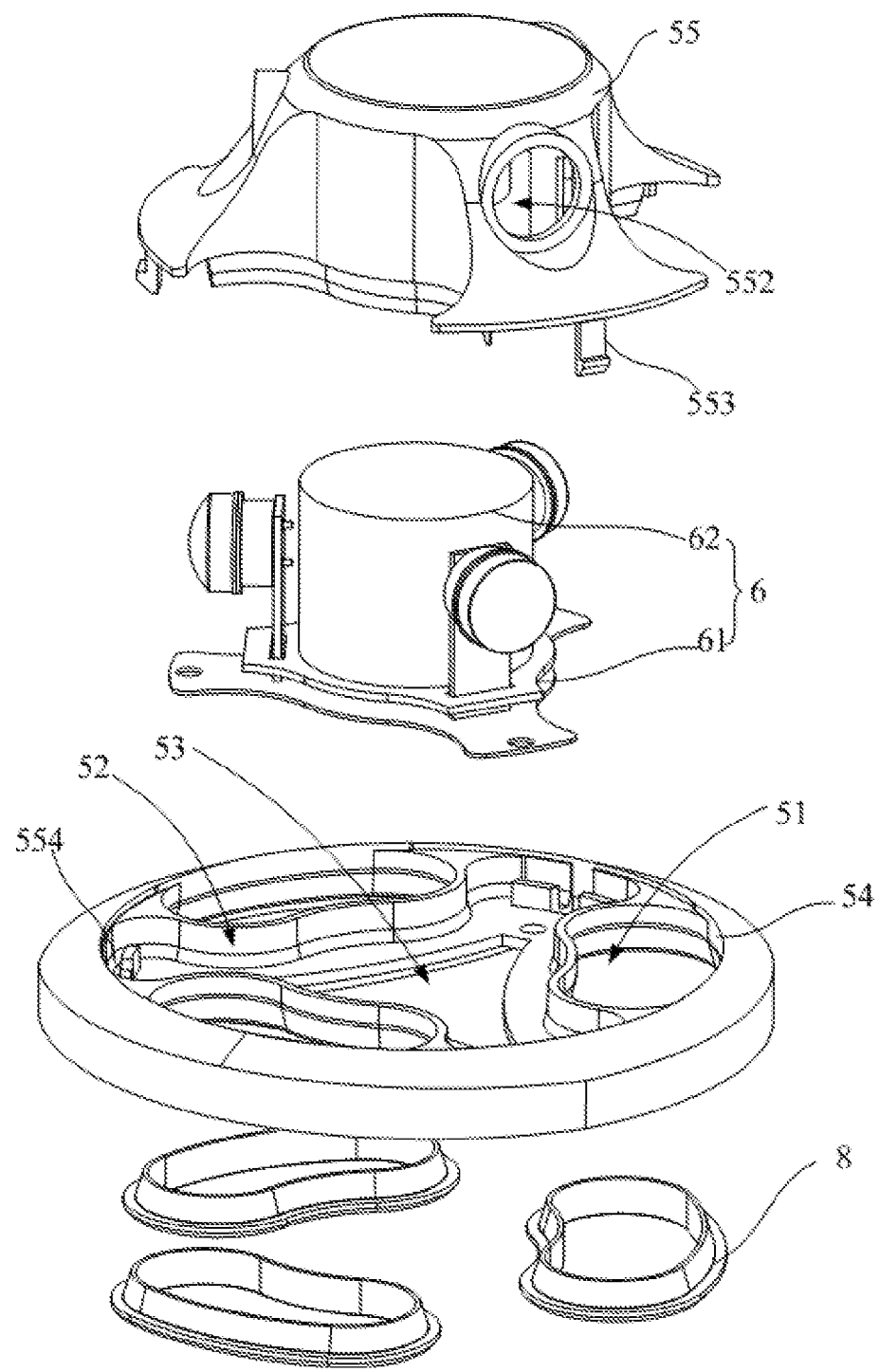
FIG. 5 is a schematic diagram showing the assembly structure of inductive component in FIG. 4.
Figure 6:
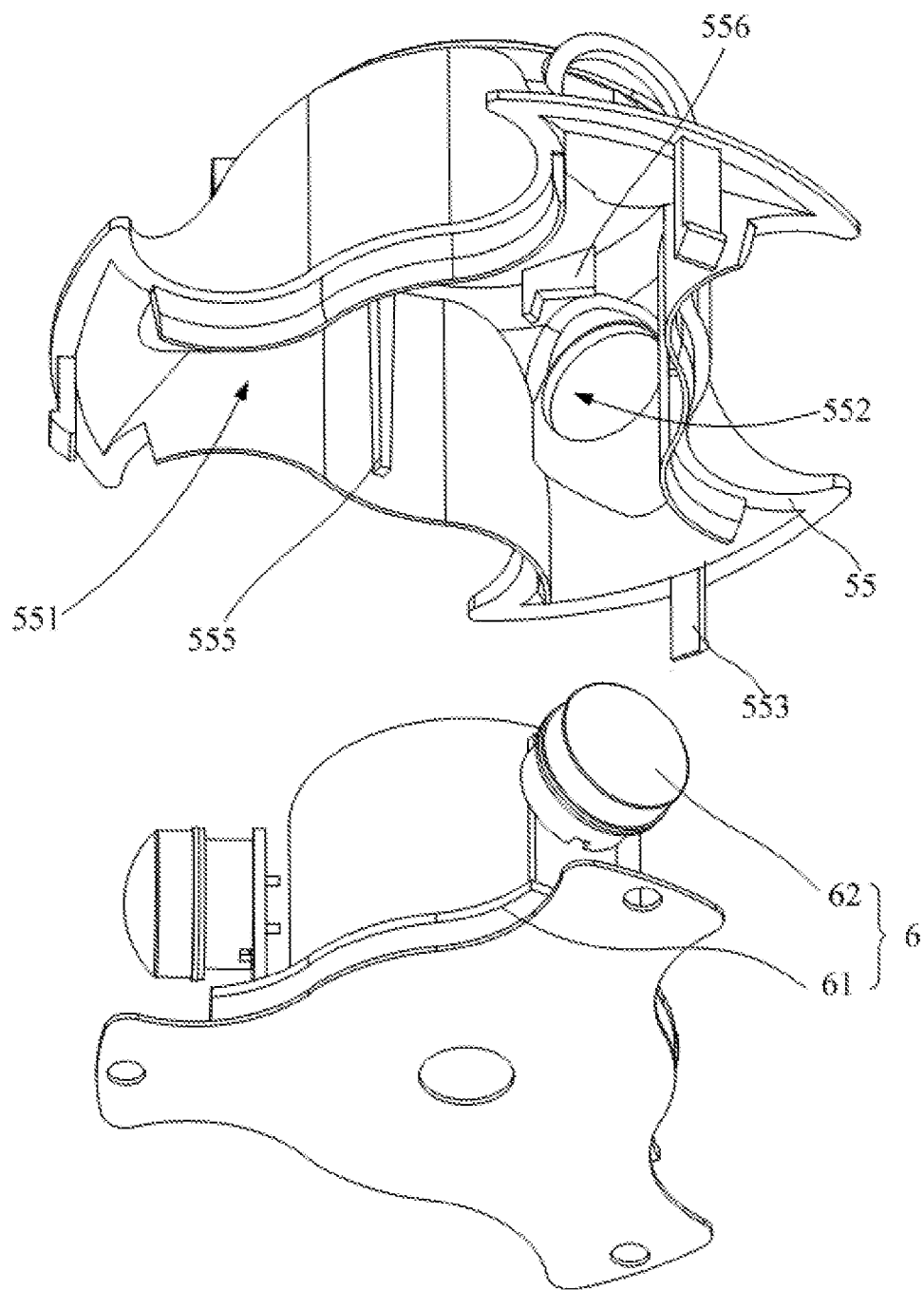
FIG. 6 is a schematic diagram showing the assembly structure of inductive component in FIG. 5 from another perspective.
Figure 7:
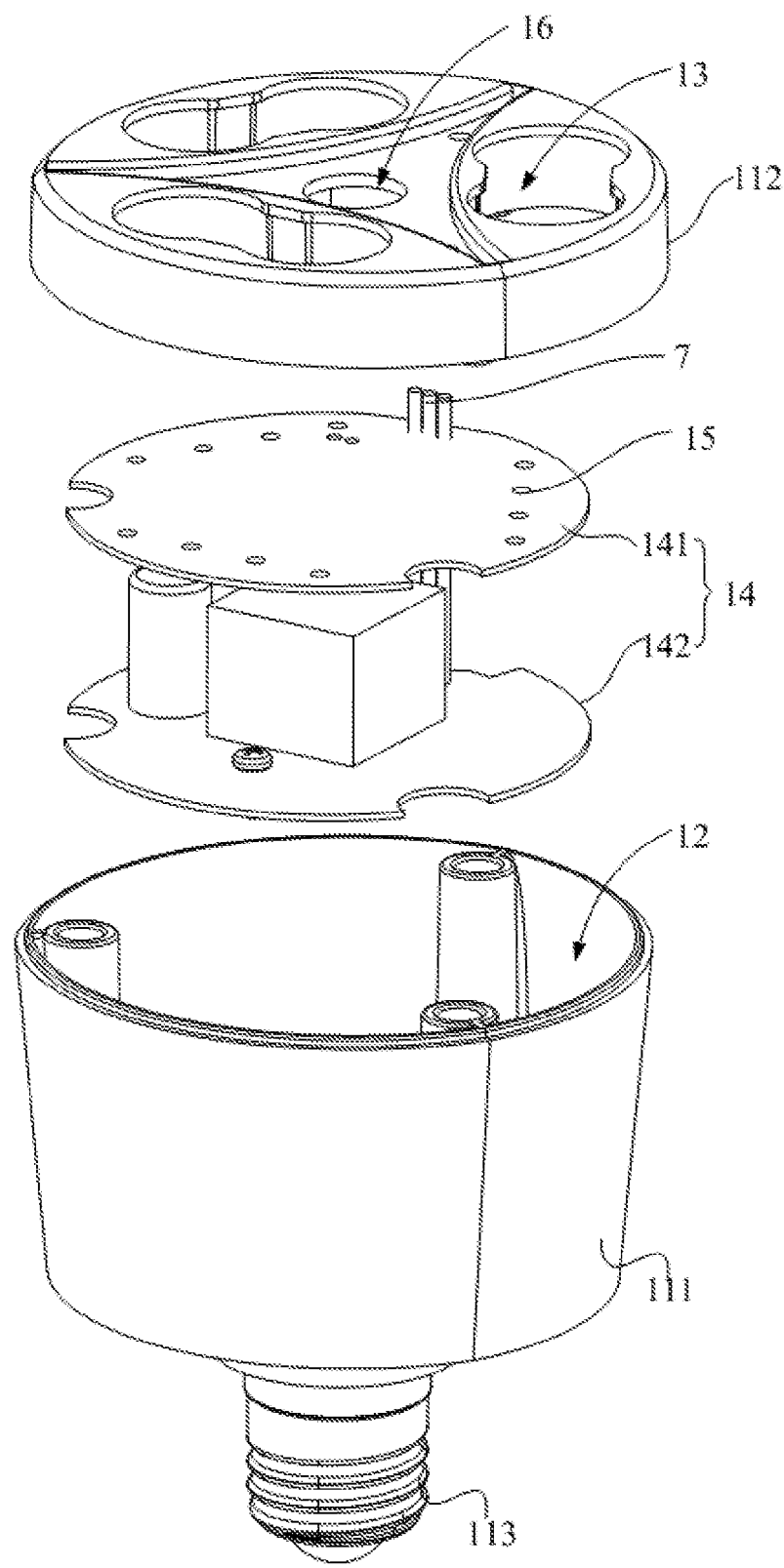
FIG. 7 is a schematic diagram showing the assembly structure of base in FIG. 1.
Figure 8:
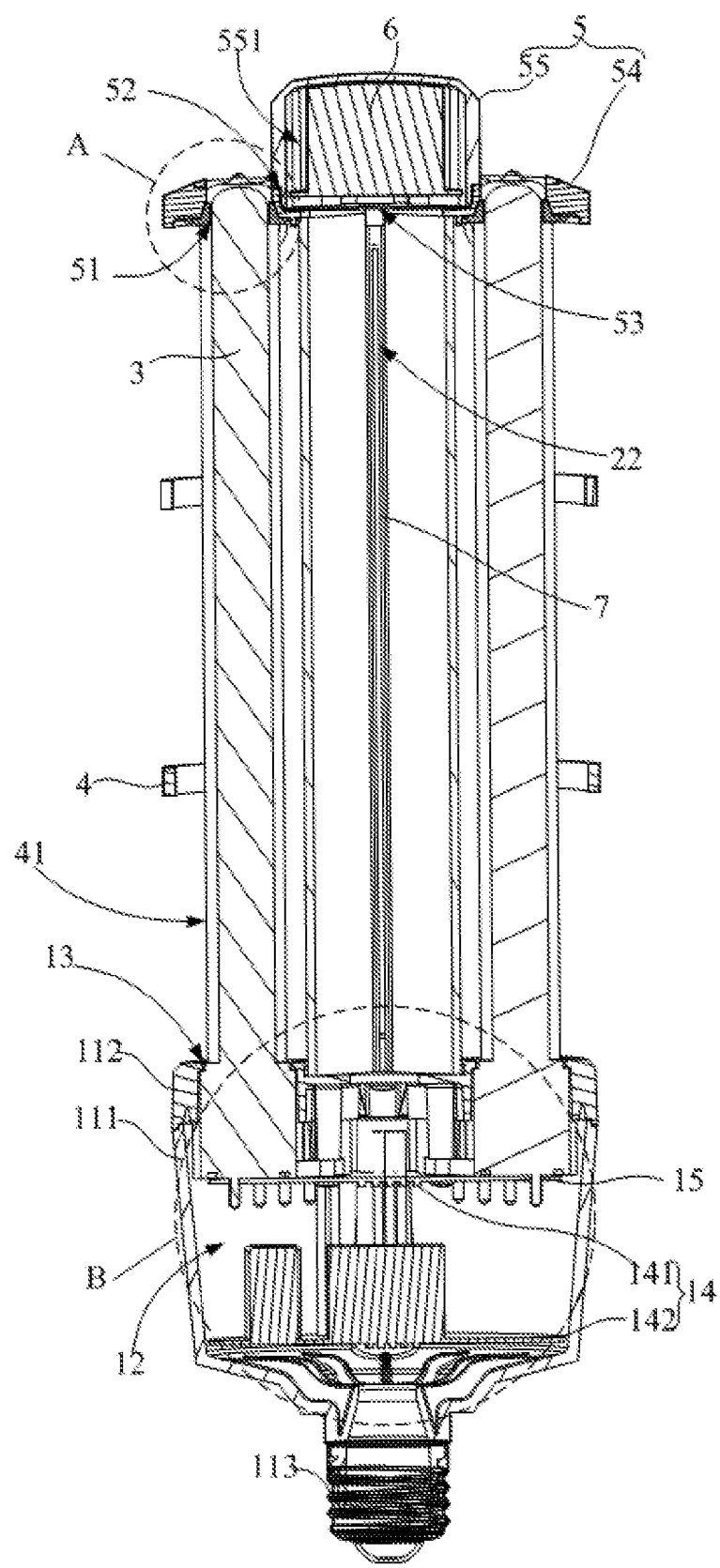
FIG. 8 is a schematic diagram showing the cross-sectional structure of UV light in FIG. 1.
Figure 9:
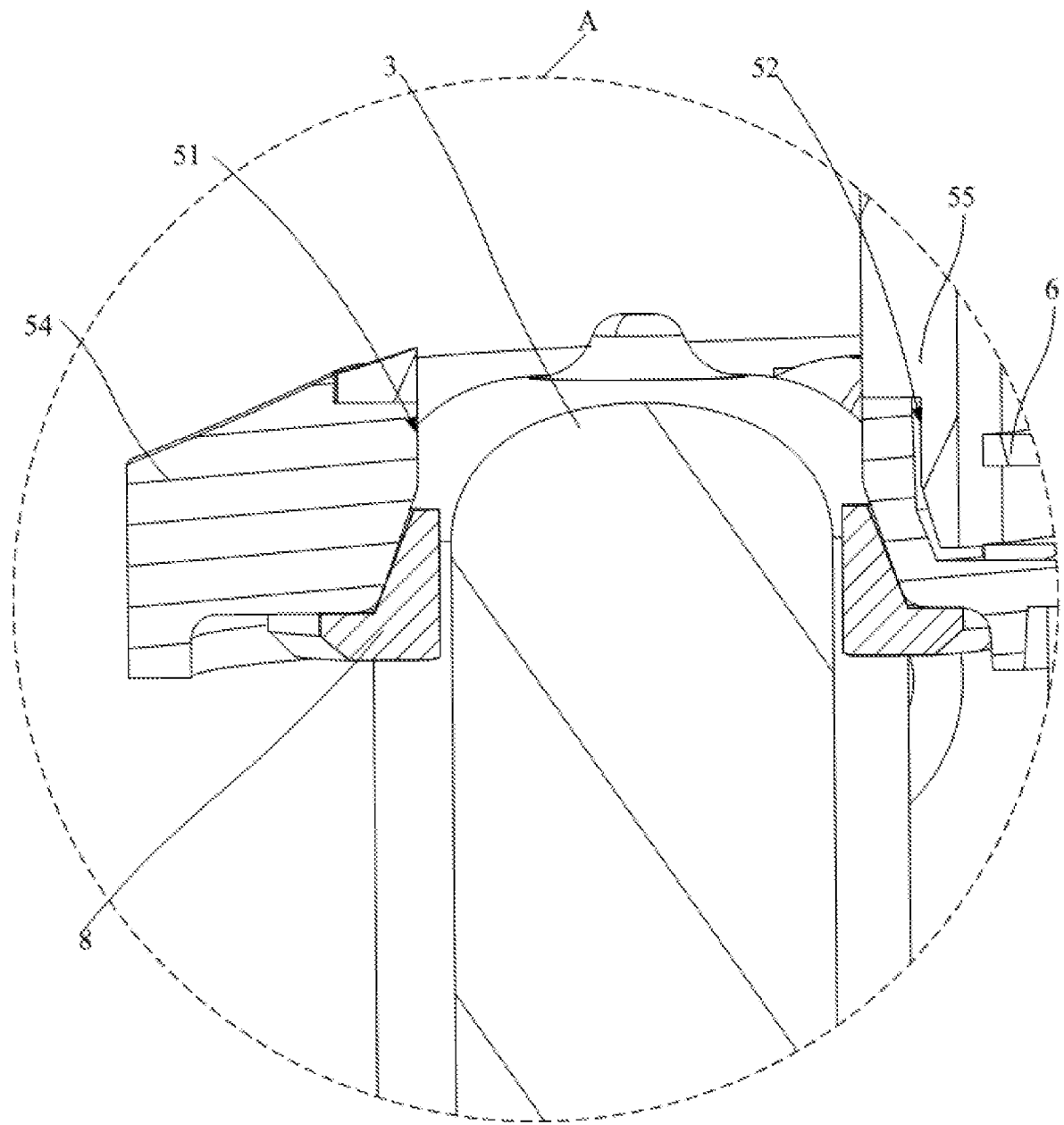
FIG. 9 is a partial enlarged drawing of section A in FIG. 8.
Figure 10:
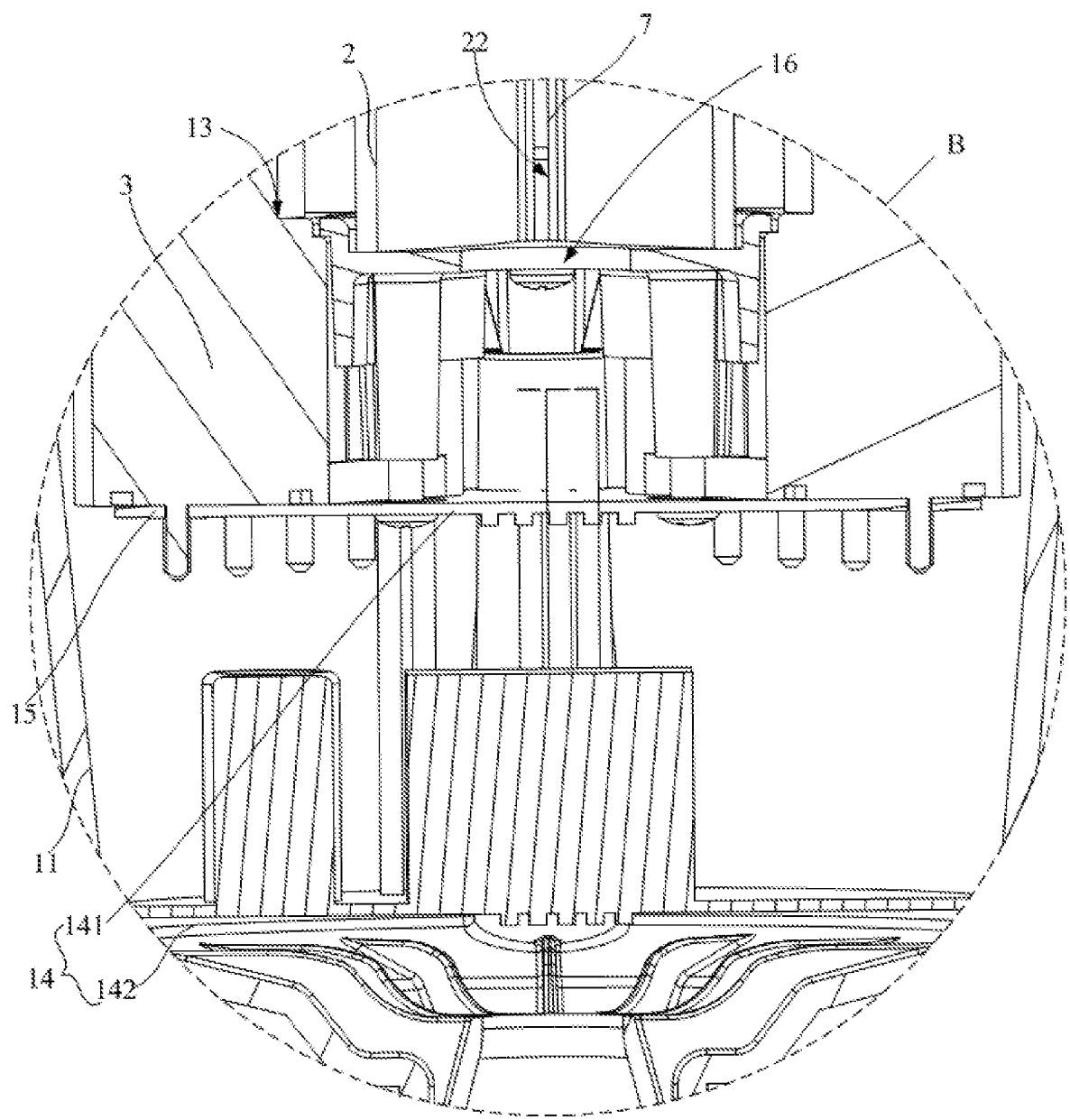
FIG. 10 is a partial enlarged drawing of section B in FIG. 8. The implementation, functional characteristics and advantages of the invention will be further illustrated hereinafter in conjunction with the embodiments and accompanying drawings.

This invention provides a UV light. Refer to FIG. 1, it is a schematic diagram showing the structure of an embodiment of UV light in the invention; Refer to FIG. 2, it is a schematic diagram showing the assembly structure of UV light in FIG. 1; Refer to FIG. 3, it is a schematic diagram showing the assembly structure of base and reflex lamp housing in FIG. 1; FIG. 4 is another schematic diagram showing the assembly structure of base and reflex lamp housing in FIG. 3; Refer to FIG. 5, it is a schematic diagram showing the assembly structure of inductive component in FIG. 4; Refer to FIG. 6, it is a schematic diagram showing the assembly structure of inductive component in FIG. 5 from another perspective; Refer to FIG. 7, it is a schematic diagram showing the assembly structure of base in FIG. 1; Refer to FIG. 8, it is a schematic diagram showing the cross-sectional structure of UV light in FIG. 1; Refer to FIG. 9, it is a partial enlarged drawing of section A in FIG. 8; Refer to FIG. 10, it is a partial enlarged drawing of section B in FIG. 8.

In the embodiment of this invention, as shown in FIG. 1 and according to FIG. 2, FIG. 3 and FIG. 4, this UV light is used for sending ultraviolet rays to realize sterilization of environments and/or articles. the UV light comprises: base 1, reflex lamp housing 2 and several UV modules 3, wherein, reflex lamp housing 2 is provided on base 1, several UV modules 3 are provided on reflex lamp housing 2 or base 1 and connect to base 1 electrically, several UV modules 3 are provided nearby reflex lamp housing 2, reflex lamp housing 2 is used for reflecting ultraviolet rays to make all the ultraviolet rays generated by several UV modules 3 be reflected to the environment and/or articles, avoiding waste of energy.

In an embodiment of this invention, base 1 and reflex lamp housing 2 are carriers for installing UV module 3. Understandably, base 1 is provided with a lamp cap 113 which is used for connecting the base to make the lamp cap 113 work together with the base to provide power to the base 1 to light several UV modules 3. Wherein, the lamp cap 113 is a metal contact.

In an embodiment of this invention, reflex lamp housing 2 is provided around base 1, the periphery of reflex lamp housing 2 is provided with several containing grooves 21, and the inner wall of each of containing grooves 21 is provided as a reflective panel; several UV modules 3 are provided in several containing grooves 21 and connect with base 1 electrically, and each of UV modules 3 is contained in a containing groove 21. Understandably, the inner wall of containing groove 21 can be provided with polishing treatment or electroplating treatment to form a reflective panel; when several UV modules 3 work, each of several UV modules 3 sends ultraviolet rays which are reflected by the corresponding containing groove 21 to make ultraviolet irradiate to all direction of reflex lamp housing 2, realizing effective sterilization of environments and/or articles.

In this embodiment, reflex lamp housing 2 is provided around base 1, the periphery of reflex lamp housing 2 is provided with several containing grooves 21, and the inner wall of each of containing grooves 21 is provided as a reflective panel; wherein, several the UV modules 3 are provided in several containing grooves 21, that is, UV modules 3 can connect to the base 1 and/or reflex lamp housing 2, several the UV modules 3 connect to the base 1 electrically and are contained in several containing grooves 21, taking the base 1 as the connection base of accessing power, the base 1 can provide power for several UV modules 3, and several UV modules 3 are provided in several containing grooves 21 to send ultraviolet rays. Understandably, base 1 is a connection base, a reflex lamp housing 2 is provided around base 1 to reduce the possibility that ultraviolet rays irradiate onto the base 1, so that ultraviolet rays can contact with air and articles in the environment sufficiently to improve the sterilization and disinfection efficiency; in another aspect, several UV modules 3 send ultraviolet rays to enhance UV illumination within the unit time and enhance the coverage of rays of light, improve the UV sterilization efficiency and reduce UV sterilization time; in yet another aspect, the periphery of reflex lamp housing 2 is provided with several containing grooves 21, each of containing grooves 21 inside is provided with a UV module, so that several UV modules 3 are provided around the reflex lamp housing 2, avoiding parallel setting of several UV modules 3, reducing dimensions of UV light and realizing a compact structure of the UV light; in yet another aspect, containing groove 21 is provided as a reflective panel, so that after several UV modules 3 send ultraviolet rays, ultraviolet rays can be reflected by the inner wall of containing groove 21 of reflex lamp housing 2 to the environment to realize that the environment around UV light can be illuminated by ultraviolet rays, illumination of ultraviolet rays is improved, and the sterilization effect is improved.

In one embodiment of this invention, several UV modules 3 are provided on base 1 or nearby reflex lamp housing 2;

when several UV modules 3 are provided on base 1, base 1 can be provided with an installation cavity 12 and several offsetting holes 13 connecting to the installation cavity 12, base 1 can comprise circuit component 14 provided in installation cavity 12, one end of each of several UV modules 3 connects to the inner wall of corresponding offsetting hole 13 and connects to circuit component 14 electrically.

When several UV modules 3 are provided on reflex lamp housing 2, reflex lamp housing 2 can be provided with several locating parts to clamp several UV modules 3, so that several UV modules 3 can be provided on reflex lamp housing 2. Wherein, locating parts can be locating buckles (not shown in the drawing).

Optionally, UV module 3 is a UV fluorescent tube; or, UV module 3 is UV LED lamp.

In one embodiment of this invention, UV module 4 is UV fluorescent tube. The ultraviolet ray radiation efficiency of UV fluorescent tube is much higher than that of UV LED lamp, and the price of the former is cheaper.

Optionally, the power of UV fluorescent tube can be 60 W or 78 W; the power can be altered according to the actual working scene.

In one embodiment of this invention, reflex lamp housing 2 can be an aluminum alloy workpiece, on the surface of which several containing grooves 21 are formed through processing. Optionally, reflex lamp housing 2 in the sleeve shape can be formed in the way of extrusion molding, secondary processing can be carried out on the surface of reflex lamp housing 2 to form several containing grooves 21 which will be polished or plated to form reflective panels.

Optionally, reflex lamp housing 2 can be made of plastic; that is, reflex lamp housing 2 and several containing grooves 21 are formed in the way of integral injection molding, and coating or electroplating is applied to the surface of plastic workpieces to form reflective panels.

In one embodiment of this invention, according to FIG. 2, FIG. 3 and FIG. 4, containing groove 21 is a sinking tank structure. that is, under the premise that containing groove 21 can reflect ultraviolet ray, the shape of the cross section of containing groove 21 is not restricted.

In one embodiment of this invention, according to FIG. 2, FIG. 3 and FIG. 4, the inner wall of containing groove 21 is in a cambered shape; that is, after rays of light arrives on the cambered surface, rays of light can be reflected by the cambered surface, ultraviolet rays can be reflected outward at a certain angle, and then light is reflected to the area which just faces containing groove 21 to improve the sterilization efficiency.

In one embodiment of this invention, according to FIG. 2, FIG. 3 and FIG. 4, the UV light also comprises at least a protective lantern ring 4 provided on reflex lamp housing 2 and provided at intervals with base 1 to form a light access area 41 in an enclosure way.

In this embodiment, protective lantern ring 4 is provided around reflex lamp housing 2, the periphery of reflex lamp housing 2 is provided with several containing grooves 21, so that protective lantern ring 4 can span the notch of several containing grooves 21 and protective lantern ring 4 can partially cover the notch of containing groove 21; that is, protective lantern ring 4 can serve as a shielding part to effectively protect UV module 3 from collision of external articles and improve the stability of UV light.

Optionally, protective lantern ring 4 can be made of plastic or metal, which is not restricted under the premise that protective lantern ring 4 can serve as a shielding part to protect UV module 3 from collision of external articles.

When protective lantern ring 4 is made of plastic, protective lantern ring 4 can be made into an annular shape in the way of primary modeling or secondary modeling, and then protective lantern ring 4 is provided around reflex lamp housing 2; wherein, protective lantern ring 4 and reflex lamp housing 2 can be connected in the way of dead connection or dismountable connection. In other words, protective lantern ring 4 can be made of elastic materials, the inner wall of protective lantern ring 4 is against the periphery of reflex lamp housing 2, or the inner wall of protective lantern ring 4 is provided with threads, the outer wall of reflex lamp housing 2 is also provided with corresponding threads, and protective lantern ring 4 and reflex lamp housing 2 connect through threads; no restriction is given here under the premise that protective lantern ring 4 can be used for shielding UV module 3 from collision of external articles.

When protective lantern ring 4 is made of metal, annular protective lantern ring 4 can be cut from one tube material, and protective lantern rings 4 are provided around reflex lamp housing 2. Wherein, protective lantern ring 4 and reflex lamp housing 2 can connect in the way of interference fit or through welding, which is not restricted under the premise that protective lantern ring 4 can be used for shielding UV module 3 from collision of external articles.

In one embodiment of this invention, UV light also comprises several protective lantern rings 4 provided on reflex lamp housing 2, two neighboring protective lantern rings 4 are provided at intervals, protective lantern rings 4 and base 1 are provided at intervals to form light access area 41. In this embodiment, several protective lantern rings 4 are provided at intervals, effectively protecting UV module 3.

In one embodiment of this invention, the periphery of reflex lamp housing 2 is provided with three containing grooves 21; in this embodiment, accordingly, three containing grooves 21 can contain three UV modules 3 respectively, so that ultraviolet rays are sent through three UV modules 3, realizing 360° sterilization around the periphery of reflex lamp housing 2.

In one embodiment of this invention, reflex lamp housing 2 is made of aluminum alloy; aluminum alloy is of certain extensibility, so that it can be processed into reflex lamp housing 2 to improve the production efficiency; in another aspect, aluminum alloy is of strong heat conduction performance which can realize heat dissipation of UV module 3.

In one embodiment of this invention, protective lantern ring 4 is made of aluminum alloy. aluminum alloy is of certain extensibility, so that it can be processed into protective lantern ring 4 to improve the production efficiency; in another aspect, aluminum alloy is of strong heat conduction performance which can realize heat dissipation of UV module 3.

In one embodiment of this invention, reflex lamp housing 2 is of a sleeve structure; in this embodiment, it can be deemed as that reflex lamp housing 2 is of a sleeve structure out of one tube material through cutting, several containing grooves 21 are formed on the circumferential direction of reflex lamp housing 2 in the way of extrusion molding. In other words, the area of all the cross sections of reflex lamp housing 2 is the same, protecting UV module 3 from damage of the convex inner wall of containing groove 21 and improving the installation stability of UV module 3.

In one embodiment of this invention, protective lantern ring 4 is of a sleeve structure. In this embodiment, it can be considered that protective lantern ring 4 is an annular structure out of a tube material through cutting. Several protective lantern rings 4 can be out of one tube material through cutting, simplifying the production process of protective lantern ring 4, improving the UV light production efficiency and reducing the cost of components.

In one embodiment of this invention, according to FIG. 3, FIG. 4 and FIG. 5, the UV light also comprises support plate 5 provided on one end of reflex lamp housing 2 away from base 1 and provided with locating hole 51 corresponding to each of containing grooves 21; one end of each of UV modules 3 away from base 1 goes through locating hole 51.

In this embodiment, after one end of UV module 3 connects to base 1, the other end of UV module 3 will suspend. To enhance the connection strength between UV module 3 and base 1 as well as UV module 3 and reflex lamp housing 2, a structure of support plate 5 is installed on one end of reflex lamp housing 2 away from base 1. Support plate 5 is provided with locating hole 51 corresponding to UV module 3. Partial UV module 3 passes through locating hole 51 to position both ends of UV module 3 and improve the installation stability of UV module 3.

Optionally, support plate 5 and reflex lamp housing 2 can be connected with bolts or screws.

In one embodiment of this invention, according to FIG. 5, FIG. 8 and FIG. 9, the UV light also comprises several elastic washers 8, and each of elastic washers 8 is provided in one locating hole 51; UV module 3 goes through locating hole 51, elastic washer 8 is clamped between UV module 3 and locating hole 51.

In this embodiment, elastic washer 8 is provided around the inner wall of locating hole 51, elastic washer 8 serves as a buffer medium to protect UV module 3 from damage; wherein, elastic washer 8 is made of elastic materials, such as plastic or silica gel.

In one embodiment of this invention, according to FIG. 1, FIG. 5 and FIG. 6, UV light also comprises inductive component 6 provided on one side of support plate away from reflex lamp housing 2 and connecting to base 1 electrically via lead 7, so that human bodies can be sensed by inductive component 6. When there are no people in the environment, the UV light can carry out sterilization and disinfection automatically, improving the safety in use.

In practical application of this embodiment, if human bodies are exposed to strong ultraviolet rays for a long time, people's skin or eyes will be likely to be damaged; so, to improve the usage safety of UV light, an inductive component 6 is provided by connecting to base 1 electrically to sense human bodies. Wherein, inductive component 6 can comprise microwave sensors and/or IR sensors.

When inductive component 6 sense approaching human bodies, UV light will be turned off automatically, and then several UV modules 3 will stop working; when inductive component 6 does not sense human bodies, there are no people in the environment, UV light will be turned on automatically, and several UV modules 3 will start to work.

When the UV light works, a period of working time can be preset by users, and then sterilization and disinfection will be carried out within this period of time set. Wherein, the working time value can be any value, such as: 30 min, 60 min, 90 min and 120 min, etc.

In one embodiment of this invention, according to FIG. 5 and FIG. 6, one side of support plate 5 back on to reflex lamp housing 2 is provided with mounting groove 52 and through-hole 53 connecting to mounting groove 52, reflex lamp housing 2 is also provided with avoiding hole 22 connecting through-hole 53, inductive component 6 is provided in mounting groove 52, and inductive component 6 connects to base 1 via lead 7 passing through avoiding hole 22 and through-hole 53.

In this embodiment, reflex lamp housing 2 is provided with avoiding hole 22, inductive component 6 can connects to base 1 via lead 7 passing through avoiding hole 22 of reflex lamp housing 2 to avoid damage of lead 7 caused by overheat arising from that lead 7 passes containing groove 21; Meanwhile, it can avoid external wiring of reflex lamp housing 2, achieving a beautiful product appearance.

In one embodiment of this invention, according to FIG. 5 and FIG. 6, inductive component 6 comprises the third circuit board 61 provided on mounting groove 52 and several sensors 62 provided on the third circuit board 61, the third circuit board 61 connects to circuit component 14 via lead 7, and several sensors 62 are provided on one side of the third circuit board 61 back on to support plate 5. Wherein, sensors 62 can be IR sensors or microwave sensors.

Optionally, support plate 5 can be made of metal, such as aluminum alloy. UV light also comprises an insulation pad provided in mounting groove 52 and clamped between the bottom wall of mounting groove 52 and the third circuit board 61 of inductive component 6 to avoid short circuit of components on the third circuit board 61.

In one embodiment of this invention, according to FIG. 5 and FIG. 6, support plate 5 comprises support cover 54 and housing 55, support cover 54 is provided with mounting groove 52, housing 55 connects to the notch of mounting groove 52, housing 55 is provided with locating groove 551 and mounting hole 552 connecting to locating groove 551, when support cover 54 and housing 55 connect, the notch of locating groove 551 is provided corresponding to that of mounting groove 52. The IR sensor is provided corresponding to one mounting hole 552.

Optionally, according to FIG. 6, the periphery of support cover 54 can be provided with several mounting holes 552, inductive component 6 comprises several IR sensors, and each of the IR sensors is provided corresponding to one mounting hole 552. In another aspect, when sensors 62 are microwave sensors, support cover 54 can be made of plastic, microwave sensors can send microwaves to sense human bodies to avoid hole opening on support cover 54 and reduce processing procedures.

Optionally, according to FIG. 6, the inner wall of housing 55 is provided with several protruding support bars 555 to enhance the structural strength of support cover 54. In another aspect, when support cover 54 and housing 55 connect, one end of support bar 555 nearby the support cover 54 can be against the third circuit board 61 to further locate the third circuit board 61.

Optionally, according to FIG. 6, the bottom wall of locating groove 551 is provided with several protruding locating bars 556, each of locating bars 556 is provided nearby each of mounting holes 552, locating bars 556 align with mounting holes 552, forming a locating scape (not shown in the drawing) with the inner wall where locating hole 51 is, IR sensors are provided on support cover 54, and IR sensors are located within the locating space. In other words, the periphery of IR sensors can be provided with a locating table (not shown in the drawing), both sides of the locating table are against locating bar 556 and the inner wall where locating hole 51 is.

In one embodiment of this invention, locating groove 551 is used for providing an offsetting space for the third circuit board 61 and sensors.

In one embodiment of this invention, according to FIG. 5 and FIG. 6, housing 55 is provided with a fastening part 553, the inner wall of mounting groove 52 is provided with a buckle placement position 554, fastening part 553 is snap-fitted with buckle placement position 554 to make housing 55 connects to support cover 54.

In one embodiment of this invention, as shown in FIG. 7, FIG. 8 and FIG. 10, and base 1 comprises: lamp housing 11 provided with installation cavity 12 and several offsetting holes 13 connecting installation cavity 12; wire hole 16 through which lead 7 may pass; and circuit component 14 provided in installation cavity 12 and provided with connection end 15 corresponding to each of offsetting holes 13; reflex lamp housing 2 connects to lamp housing, each of containing grooves 21 is provided corresponding to each of offsetting hole 13, each of UV modules 3 passes through each of offsetting holes 13 and connects to connection end 15 electrically.

In this embodiment, lamp housing 11 is provided with a lamp cap 113, lamp cap 113 connects to circuit component 14 electrically to access the power grid to provide power for circuit component 14. Wherein, the lamp cap 11 is a metal contact. In another aspect, circuit component 14 is provided with connection end 15 corresponding to each of offsetting holes 13, each of UV modules 3 connects to connection end 15 electrically to avoid connection between circuit component 14 and UV module 3 via cables, simplifying the circuit structure.

Optionally, connection end 15 can comprise several metal jacks, UV module 3 is provided with metal pins provided in metal jacks to make UV module 3 and circuit component 14 connect electrically.

In one embodiment of this invention, according to FIG. 7, FIG. 8 and FIG. 10, lamp housing 11 also comprises bottom shell 111, upper cover 112 and lamp cap 113, bottom shell 111 is provided with a slot (not shown in the drawing) and mounting opening (not shown in the drawing) connecting to the slot, lamp cap 113 and bottom shell 111 connect, forming installation cavity 12, and upper cover 112 is provided with several offsetting holes 13. Wherein, lamp cap 113 is a metal contact use for electrical connection with the base to access the power grid.

The circuit component 14 comprises the first circuit board 141 and the second circuit board 142 contained in installation cavity 12, wherein, the first circuit board 141 connect to the second circuit board 142, the first circuit board 141 connects the inner wall of tank, the second circuit board 142 is provided on one side of upper cover 112 facing bottom shell 111, the second circuit board 142 is provided with connection end 15, and the first circuit board 141 is provided with a power adapter.

In this embodiment, in installation cavity 12 of lamp housing 11, the first circuit board 141 and the second circuit board 142 connecting to the first circuit board 141 are provided, the first circuit board 141 is provided with a power adapter, and the second circuit board 142 is provided with connection end 15; understandably, the first circuit board 141 is provided with a power adapter, and the second circuit board 142 is provided with connection end 15, so that the power adapter and connection end 15 can be provided independently, the first circuit board 141 and the second circuit board 142 which are provided independently divide several functions of circuit component 14 effective to simplify functions of one circuit board, lower production difficulties and improve the production efficiency; meanwhile, disassembly and assembly of the first circuit board 141 and the second circuit board 142 can be carried out independently, improving the maintainability of circuit component 14. in another aspect, the first circuit board 141 and the second circuit board 142 are provided at intervals, leaving clearance between the first circuit board 141 and the second circuit board 142 to enhance the heat dissipation effect. In yet another aspect, the first circuit board 141 is on one side of the second circuit board 142 relatively, making the projection area of the first circuit board 141 and that of the second circuit board 142 overlap to reduce the transverse occupation area of base 1 and improve the structure compactness of base 1.

Optionally, UV module 3 is a UV fluorescent tube; UV fluorescent tube is provided with several metal pins, enabling the UV fluorescent tube to be plugged into connection end 15 of the second circuit board 142 via several metal pins. Wherein, connection end 15 is provided with several metal jacks, that is, the second circuit board 142 is provided with several through-holes whose inner walls are provided with metal coating.

This invention also provides a sterilization system comprising a remote control (not shown in the drawing), and a UV light. The specific structure of the UV light can refer to the afore the embodiments. Since the sterilization system adopts all the technical solutions of all the afore the embodiments, at least the system can achieve all the beneficial effects of all the technical solutions of afore the embodiments, so unnecessary details will not be given here. Wherein, the remote control connects to base 1 of the UV light for communication.

In this embodiment, the remote control connects to the UV light in the wireless way, so that the remote control can control the UV light as needed, improving the adaptability of UV light. Wherein, circuit component 14 of the UV light can be integrated with a wireless receiving & sending module for receiving types of wireless signals, such as: IR signals, RF signals, etc.

Optionally, the remote control can be a regular model of remote control or terminal equipment, such as mobile phone, computer, etc.

Optionally, when the wireless receiving & sending module is an IR module, the enclosure covering on the wireless receiving & sending module should be made of transparent or semi-transparent materials.

In another aspect, the wireless receiving & sending module can also be provided on one side of support plate 5 away from the reflex lamp housing 2 and provided nearby inductive component 6. Or, the wireless receiving & sending module can also be integrated with inductive component 6.

the description is only the preferred embodiment of the invention, and it is not for this reason that the patent scope of the invention is limited. Any equivalent structural transformation made by using the description of the invention and the drawing, or direct/indirect application in other related innovation technical fields under the inventive concept of the invention, is included in the patent protection scope of the invention.

What is claimed is:

1. A UV light comprising:
   a base;
   a reflex lamp housing provided on the base, a periphery of the reflex lamp housing provided with several containing grooves, an inner wall of each of the containing grooves provided as a reflective panel; and
   at least one UV emitter provided in each of the several containing grooves and connected electrically to the base,
   wherein the UV light further comprises a support plate provided at a distal end of the reflex lamp housing opposite that of the base,
   wherein at least one sensor is mounted on a side of the support plate opposite the reflex lamp housing,
   wherein the at least one sensor is electrically connected to the base via a lead,
   wherein the support plate comprises a support cover connected to a support housing,
   wherein the support housing is provided with at least one locating groove with a corresponding mounting hole in which one of the at least one sensor is located,
   wherein each of the at least one locating groove is provided with a locating bar aligned with the corresponding mounting hole, the locating bar comprising a first guiding incline and a second guiding incline arranged at an angle to each other for aligning the one of the at least one sensor located in the corresponding mounting hole, and
   wherein each of the at least one sensor are provided with a locating table which is configured to rest against a corresponding locating bar.

2. The UV light as claimed in claim 1, wherein the inner wall of each of the containing grooves is in a cambered shape.

3. The UV light as claimed in claim 1, wherein the UV light further comprises at least one protective lantern ring provided around the reflex lamp housing and provided at intervals relative to the base to form a light access area.

4. The UV light as claimed in claim 3, wherein the periphery of the reflex lamp housing is provided with three containing grooves.

5. The UV light as claimed in claim 3, wherein the reflex lamp housing is made of aluminum alloy.

6. The UV light as claimed in claim 3, wherein the protective lantern ring is made of aluminum alloy.

7. The UV light as claimed in claim 3, wherein the reflex lamp housing is formed as a sleeve.

8. The UV light as claimed in claim 3, wherein the protective lantern ring is formed as a sleeve.

9. The UV light as claimed in claim 1, wherein the support plate is provided with a locating hole corresponding to each of the several containing grooves, and
   wherein one or more of the at least one UV emitter provided in each of the several containing grooves protrudes through a corresponding locating hole.

10. The UV light as claimed in claim 9, wherein each locating hole is provided with an elastic washer which is clamped between the locating hole and the one or more of the at least one UV emitter which protrudes through the locating hole.

11. The UV light as claimed in claim 1, wherein the base further comprises a housing provided with an installation cavity and several offsetting holes connecting the installation cavity,
    wherein circuitry components are provided in the installation cavity and connect with a connection end corresponding to each of the offsetting holes;holes, and
    wherein the reflex lamp housing connects to the lamp housing, each of the containing grooves provided with a corresponding one of the offsetting holes, the UV emitters passing through the offsetting holes to achieve an electrical connection.

12. A sterilization system comprising the UV light as claimed in claim 1 and a remote control which wireles sly connects and communicates with of the UV light.

13. The UV light as claimed in claim 1, wherein the base comprises a threaded metal contact which is insertable into a socket to connect the UV light to electrical power.

14. The UV light as claimed in claim 1, wherein the at least one sensor comprises at least one of a microwave sensor and an IR sensor.

* * * * *